United States Patent
Deane

(10) Patent No.: US 11,464,728 B1
(45) Date of Patent: *Oct. 11, 2022

(54) LIP CARE COMPOSITION

(71) Applicant: Jeffrey Alan Deane, Los Angeles, CA (US)

(72) Inventor: Jeffrey Alan Deane, Los Angeles, CA (US)

(*) Notice: Subject to any disclaimer, the term of this patent is extended or adjusted under 35 U.S.C. 154(b) by 4 days.

This patent is subject to a terminal disclaimer.

(21) Appl. No.: 16/576,607

(22) Filed: Sep. 19, 2019

Related U.S. Application Data

(60) Provisional application No. 62/774,026, filed on Nov. 30, 2018.

(51) Int. Cl.
*A61K 8/67* (2006.01)
*A61K 8/92* (2006.01)
*A61K 8/362* (2006.01)
*A61Q 1/04* (2006.01)
*A61K 8/49* (2006.01)

(52) U.S. Cl.
CPC .............. *A61K 8/678* (2013.01); *A61K 8/362* (2013.01); *A61K 8/498* (2013.01); *A61K 8/922* (2013.01); *A61K 8/925* (2013.01); *A61Q 1/04* (2013.01); *A61K 2800/48* (2013.01); *A61K 2800/522* (2013.01)

(58) Field of Classification Search
None
See application file for complete search history.

(56) References Cited

U.S. PATENT DOCUMENTS

| | | | | |
|---|---|---|---|---|
| 6,001,374 A | * | 12/1999 | Nichols | A61K 8/73 424/401 |
| 2005/0266064 A1 | * | 12/2005 | McCarthy | A61K 31/401 424/450 |
| 2013/0319889 A1 | * | 12/2013 | DeSantis | A61J 1/00 206/438 |
| 2015/0374769 A1 | | 12/2015 | Hines et al. | |
| 2016/0030567 A1 | * | 2/2016 | Blakeslee | A61K 35/76 424/537 |
| 2017/0136077 A1 | | 5/2017 | Hines et al. | |
| 2018/0193250 A1 | | 7/2018 | Faller et al. | |

OTHER PUBLICATIONS

Sharma, Tanya, "Korres Lemon Lip Scrub", 2019, accessed online on Sep. 19, 2019 at: https://makeup.lovetoknow.com/Korres_Lemon_Lip_Scrub.
Premier Specialties, Inc., "Natural Cosmetic Ingredients: Functional—Natural Exfoliants and Powders", accessed online on Sep. 19, 2019 at: https://www/.premierfragrances.com/natural-cosmetic-ingredients/natural-exfoliants-and-powders.
Mishra "10 best Way to Naturally Plumpy and Sexy Lips—Natural lip plumper;" https://web.archive.org/web/20170911010008/https://indiafashionblogger.com/best-way-naturally-plumpy-sexy-lips-natural-lip-plumper/—web archived version from Nov. 9, 2017.
Non-Final Office Action of the USPTO dated Mar. 23, 2021 for related U.S. Appl. No. 16/576,614.
Final Office Action of the USPTO dated Sep. 13, 2021 for related U.S. Appl. No. 16/576,614.
Non-Final Office Action of the USPTO dated Apr. 20, 2022 for related U.S. Appl. No. 16/576,614.

* cited by examiner

*Primary Examiner* — Susan Hoffman
(74) *Attorney, Agent, or Firm* — Womble Bond Dickinson (US) LLP

(57) ABSTRACT

A lip care composition including an emollient, a thickener, an antioxidant, an emulsifier, a botanical, a vitamin, a humectant, a film former, a calming agent, a sweetener and a lip plumper, the lip plumper comprising Sodium Hyaluronate in an amount of from 0.01% to 0.1% by weight, *Arnica montana* Flower Extract in an amount of from 0.01% to 0.1% by weight and Phytonadione in an amount of from 0.01% to 0.1% by weight of the total composition.

16 Claims, No Drawings

LIP CARE COMPOSITION

CROSS-REFERENCE TO RELATED APPLICATION

The application is a non-provisional application of U.S. Provisional Patent Application No. 62/774,026, filed Nov. 30, 2018, all of which is incorporated herein by reference.

FIELD

Lip care compositions. More specifically, a lip care stick, balm, or the like.

BACKGROUND

There are a wide variety of lip care products on the market. For example, one common lip care product on the market are lip balms which are contained in a lipstick-style tube and applied using the tube to the lips. Some lip balms such as ChapStick@ are formulated to prevent and/or protect chafed, chapped, sunburned, cracked, and wind burned lips. Often times, however, lip balms include ingredients such as phenol, menthol and/or salicylic acid, which have been found to actually dry out the user's lips.

SUMMARY

In one aspect, the invention is directed to a lip care composition including an emollient; a thickener; an antioxidant; an emulsifier; a botanical; a vitamin; a humectant; a film former; a calming agent; a sweetener; and a lip plumper, the lip plumper comprising Sodium Hyaluronate in an amount of from 0.01% to 0.1% by weight, *Arnica montana* Flower Extract in an amount of from 0.01% to 0.1% by weight and Phytonadione in an amount of from 0.01% to 0.1% by weight of the total composition. The lip care composition may further include a colorant. The emollient may be in an amount of at least 30% by weight of the total composition. The thickener is in an amount of from 5% to 25% by weight of the total composition. The antioxidant may be in an amount of from 0.1% to 0.3% by weight of the total composition. The emulsifier may be in an amount of from 0.3% to 1% by weight of the total composition. The botanical may be in an amount of from 0.6% to 2.5% by weight of the total composition. The vitamin may be in an amount of from 0.1 to 0.6% by weight of the total composition. The emollient may include a combination of Vegetable Oil, Paraffinum Liquidum, *Helianthus annuus* Seed Oil, *Ricinus communis* Seed Oil, *Butyrospermum parkii* (Shea) Butter Extract Unsaponifiables, Mango Butter, Jojoba Esters, Hydrogenated Vegetable Oil, Squalene, *Theobroma grandiflorum* (Cupuacu) Seed Butter, *Schinziophyton rautanenii* (Mongongo) Seed Oil, *Persea gratissima* (Avocado) Oil, *Orbignya oleifera* Seed (Babassu Nut) Oil, Hydrogenated *Moringa* Oil Esters, *Punica granatum* (Pomegranate) Seed Oil, *Oenothera biennis* (Evening Primrose) Oil, and *Camellia kissi* (Sasanqua) Seed Oil. The thickener may include a combination of Ozokerite Wax, Beeswax, Nylon-11, *Euphorbia* Cerifera Wax and *Copernicia cerifera* Wax. The antioxidant may include Tocopherol. The emulsifier may include Cetyl Esters. The botanical may include a combination of *Vanilla planifolia* Fruit Extract, *Avena sativa* Kernel Oil, *Lavandula angustifolia* Oil, *Aloe barbadensis* Leaf Extract and *Bambusa vulgaris* Water. The vitamin may include a combination of Tocopheryl Acetate, Beta-Sitosterol and Ascorbyl Palmitate. The humectant may include *Crambe abyssinica* Seed Oil. The film former may include Citrus *Aurantium dulcis* Peel Wax. The calming agent may include Allantoin. The sweetener may include Sucralose.

In another aspect, a composition is provided including at least 30.00 by weight Vegetable Oil; 10% to 30% by weight Paraffinum Liquidum; 10% to 30% by weight *Helianthus annuus* Seed Oil; 10% to 30% by weight *Butyrospermum parkii* Butter Unsaponifiable; 3% to 10% by weight Ozokerite Wax; 3% to 10% by weight Beeswax; 1% to 3% by weight Nylon-11; 1% to 3% by weight *Ricinus communis* Seed Oil; 03% to 1% by weight *Vanilla planifolia* Fruit Extract; 0.3% to 1% by weight Cetyl Esters; 0.3% to 1% by weight *Butyrospermum parkii* Butter Extract: 0.3% to 1% by weight *Avena sativa* Kernel Oil; 0.1% to 0.3% by weight Tocopheryl Acetate; 0.1% to 0.3% by weight Mango Butter; 0.1% to 0.3% by weight Jojoba Esters; 0.1% to 0.3% by weight *Euphorbia* Cerifera Wax; 0.1% to 0.3% by weight *Copernicia cerifera* Wax; 0.1% to 0.3% by weight Hydrogenated Vegetable Oil; 0.1% to 0.3% by weight Tocopherol; 0.01% to 0.1% by weight Iron Oxide comprising CI number 77492; 0.01% to 0.1% by weight Beta-Sitosterol; 0.01% to 0.1% by weight Mica; 0.01% to 0.1% by weight Titanium Dioxide (CAS 13663-67-7); 0.01% to 0.1% by weight *Lavandula angustifolia* Oil; 0.01% to 0.1% by weight a colorant comprising Red 33; 0.01% to 0.1% by weight Squalene; 0.01% to 0.11% by weight *Aloe barbadensis* Leaf Extract; 0.01% to 0.1% by weight Iron Oxide comprising CI number 77491; 0.01% to 0.1% by weight Ascorbyl Palmitate: 0.01% to 0.1% by weight Sucralose; 0.01% to 0.1% by weight *Theobroma grandiflorum* Seed Butter; 0.01% to 0.1% by weight *Schinziophyton rautanenii* Seed Oil; 0.01% to 0.1% by weight *Persea gratissima* Oil: 0.01% to 0.1% by weight *Orbignya oleifera* Seed Oil; 0.01% to 0.1% by weight Hydrogenated *Moringa* Oil Esters; 0.01% to 0.1% by weight *Crambe abyssinica* Seed Oil; 0.01% to 0.1% by weight *Punica granatum* Seed Oil; 0.01% to 0.1% by weight *Oenothera biennis* Oil; 0.01% to 0.1% by weight *Camellia kissi* Seed Oil: 0.01% to 0.1% by weight Citrus *Aurantium dulcis* Peel Wax; 0.01% to 0.1% by weight Allantoin; 0.01% to 0.1% by weight Red 7; 0.01% to 0.1% by weight Red 6; 0.01% to 0.1% by weight Titanium Dioxide comprising CI number 77891; 0.01% to 0.1% by weight Triethoxycaprylylsilane; 0.01% to 0.1% by weight Sodium Hyaluronate; 0.01% to 0.1% by weight *Bambusa vulgaris* Water; 0.01% to 0,1% by weight *Arnica montana* Flower Extract; 0.01% to 0,1% by weight Phytonadione; and 0.01% to 0.1% by weight Black Iron Oxide.

In another aspect, a composition is provided including at least 30% by weight Vegetable Oil; 10% to 30% by weight Paraffinum Liquidum; 10% to 30% by weight *Helianthus annuus* Seed Oil; 10% to 30% by weight *Butyrospermum parkii* Unsaponifiables; 3% to 10% by weight Ozokerite Wax; 3% to 10% by weight Beeswax; 1% to 3% by weightNylon-11; 0.3% to 1% by weight Tocopherol; 0.3% to 1% by weight Cetyl Esters; 0.3% to 1% by weight *Butyrospermum parkii* Extract; 0.3% to 1% by weight *Avena sativa* Kernel Oil; 0.1% to 0.3% by weight Tocopheryl Acetate; 0.1% to 0.3% by weight Mango Butter; 0.1% to 0.3% by weight Jojoba Esters; 0.1% to 0.3% by weight *Euphorbia* Cerifera Wax; 0.1% to 0.3% by weight *Copernicia cerifera* Wax; 0.1% to 0.3% by weight *Cocos nucifera* Oil; 0.1% to 0.3% by weight *Aloe barbadensis* Leaf Extract; 0.01% to 0.1% by weight *Melaleuca alternifolia* Leaf Oil; 0.01% to 0.1% by weight Ascorbyl Palmitate: 0.01% to 0.1% by weight *Theobroma grandiflorum* Seed Butter; 0.01% to 0.1% by weight *Schinziophyton rautanenii* Seed Oil; 0.01% to 0.1% by weight *Persea gratissima* Oil; 0.01% to 0.1% by weight *Orbignya oleifera* Seed Oil; 0.01% to 0.1% by weight Hydrogenated *Moringa* Oil Esters; 0.01% to 0,1% by weight *Crambe abyssinica* Seed Oil; 0.01% to 0.1% by weight *Punica granatum* Seed Oil; 0.01% to 0.1% by weight *Oenothera biennis* Oil; 0.01% to 0.1% by weight *Camellia kissi* Seed Oil; 0.01% to 0.1% by weight Citrus *Aurantium dulcis* Peel Wax; 0.01% to 0.1% by weight Allantoin; 0,01% to 0.1% by weight Sucralose; 0.01% to 0.1% by weight Sodium Hyaluronate; 0.01% to 0.1% by weight *Bambusa vulgaris* Water; 0.01% to 0.1% by weight *Arnica montana* Flower Extract; and 0.01% to 0.1% by weight Phytonadione.

The above summary does not include an exhaustive list of all aspects of the present invention. It is contemplated that the invention includes all compsitions that can be practiced from all suitable combinations of the various aspects summarized above, as well as those disclosed in the Detailed Description below and particularly pointed out in the claims filed with the application. Such combinations have particular advantages not specifically recited in the above summary.

DETAILED DESCRIPTION

In one embodiment, the lip care composition disclosed herein is a restorative lip care composition formulated to restore, moisturize and/or treat dry, parched lips and lock in long-lasting moisture. In some embodiments, the composition is a topical product, for example, a topical lip care product such as a lip stick, a lip balm, a lip scrub, or the like. Although representative compositions forms are disclosed, it should be understood that the composition may be in any form suitable for application to a user's lips.

The composition may include several key ingredients in amounts, which in combination, work synergistically, to care for a user's lips. For example, the key ingredients may have a restorative, a moisturizing, a lip plumping, a scrubbing, and/or an exfoliating effect, to name a few. The combination of ingredients are specifically selected and combined to form a composition, for example a lip care or treatment composition.

Lip Stick

Representatively, in one embodiment, the composition may by a lip treatment stick or balm including a synergistic combination of one or more of an emollient(s), thickener(s), botanical(s), antioxidant(s), plumping agent(s) emulsifiers(s), vitamin(s), humectant(s), film former(s), calming agent(s) and/or sweeteners(s). Additionally, the composition may include a colorant(s).

In one embodiment, the composition balances one or more emollient(s), thickeners(s), botanical(s), antioxidants(s), plumping agent(s) emulsifiers(s), vitamin(s), humectant(s), film formers(s), calming agent(s), sweeteners(s) and/or colorant(s) in amounts sufficient to provide a composition that effectively nourishes, moisturizes, restores, treats and/or plumps the lips when it is applied.

Representatively, in one aspect, the lip care composition may include, among others, ingredients and/or agents such as Paraffin, Shea butter, Beeswax, essential oils, Vitamin C & E and/or Bamboo Water, which help to moisturize, treat, restore, nourish or otherwise improve the condition of the user's lips.

Additionally, the composition may include ingredients such as Sodium Hyaluronate, *Arnica montana* Flower Extract and/or Vitamin K, which are synergistically combined to provide a lip plumping effect when applied topically to the lips. The phrase "lip plumping" is intended to refer to any increase in lip volume, and for any period of time (e.g., hours). Thus, a lip plumping agent may be any agent or ingredient that has the effect of increasing lip volume when topically applied to the lips.

Representatively, it is believed that when topically applied, Sodium Hyaluronate can facilitate the absorption or penetration of other agents, such as moisturizing agents or other agents that may have a lip plumping effect, through the skin. Thus, when combined synergistically with other agents, for example a moisturizing agent(s) or other lip plumping agents, the enhanced absorption causes an increase in lip volume for a period of time. For example, Sodium Hyaluronate may be synergistically combined with *Arnica montana* Flower Extract and/or Vitamin K to achieve maximum lip plumping.

In some aspects, the lip care composition may be a translucent lip care composition in that it does not have any added color or tint. In other aspects, the lip care composition may be a tinted lip care composition which includes an additive which adds tint or color to the lips once the composition is applied. In addition, it should be recognized that while the composition is described in some embodiments as a lip stick, the lip care composition may be in any form suitable for application to the user's lips and a container of any shape/size, and is not limited to the shape of a stick, or baton. For example, the lip care composition may be a lip balm, lip stick, lip cream, lip gel, lip gloss, or the like, that can be used in any size/shape container. The composition may be applied to the lips directly, or rubbed on the user's finger and then applied to the lips.

Representatively, in one aspect, a balanced lip care composition includes from about 60 percent (%) to about 100% by weight emollient(s), from about 6% to 21% by weight thickening agent(s), from about 0.5% to 2% by weight botanical agent(s), from about 0.3% to 1% by weight antioxidant(s), from about 0.3% to 1% by weight emulsifier(s), from about 0.1% to 0.5% by weight vitamin(s), from about 0.02% to 0.2% by weight humectant(s), from about 0.01-0.1% by weight film forming agent(s), from about 0.01% to 0.1% by weight calming agent(s), and/or from about 0.01% to 0.1% by weight sweetener(s). In addition, a combination of one or more of plumping agent(s) may be included in the composition in an amount of about 0.01% to 0.27% to effectively provide a lip plumping effect. In other embodiments, the composition can contain any one or more of the agents or ingredients disclosed herein, in any amounts and any combinations sufficient to nourish, moisturize, restore, treat and/or plumps the lips when it is applied.

Representatively, in another aspect, a balanced lip care composition including a tint includes from about 50 percent (%) to about 100% by weight emollient(s), from about 5% to 25% by weight thickening agent(s), from about 0.6% to 2.5% by weight botanical agent(s), from about 0.1% to 0.3% by weight antioxidant(s), from about 0.3% to 1% by weight emulsifier(s), from about 0.1% to 0.6% by weight vitamin(s), from about 0.02% to 0.2% by weight humectant(s), from about 0.02%-0.2% by weight film forming agent(s), from about 0.01% to 0.1% by weight calming agent(s), from about 0.01% to 0.1% by weight sweetener(s), and/or from about 0.09% to 0.9% colorant(s), in amounts sufficient to provide a composition that effectively moisturize, treat, restore, nourish or otherwise improve the condition of the user's lips. In addition, a combination of one or more of plumping agent(s) may be included in the composition in an amount of about 0.01% to 0.27% to effectively provide a lip plumping effect. In other embodiments, the composition can contain any one or more of the agents or ingredients disclosed herein, in any amounts and any combinations sufficient to nourish, moisturize, restore, treat and/or plumps the lips when it is applied.

A representative emollient(s) may include, but is not limited to, vegetable oil (virgin olive oil based), paraffinum liquidum, *Helianthus annuus* (Sunflower) Seed Oil, Butyrosperum *Parkii* (Shea Butter) Unsaponafiables, Nylon-11, Butyrosperum *Parkii* (Shea Butter) Extract, Mango (*Mangifera indica*) Butter, *Cocos nucifera* (Coconut) Oil, *Melaleuca alternifolia* (Tea Tree) Leaf Oil, *Theobroma grandiflorum* (Cupuacu) Seed Butter, Schinzeiophyton *Rautanenii* (Mongongo) Seed Oil, *Persa gratissima* (Avocado) Oil, Obignya *Oleifera* Seed (Babassu Nut) Oil, Hydrogenated *Moringa* Oil Esters, *Punica granatum* (Pomegranate) Seed Oil, *Oenothera biennis* (Evening Primrose) Oil, *Camellia kissi* (Sasanqua) Seed Oil, *Ricinus communis* (castor) seed oil, hydrogenated vegetable oil, and/or squalene.

A representative thickening agent(s) may include, but is not limited to, Ozokerite Wax, Beeswax, Nylon-11, *Euphorbia* Cerifera (Candelilla) Wax, and/or *Copernicia cerifera* (Carnauba) Wax.

The term "botanical agent" as used herein refers to plant derived products such as plant extracts and essential oils derived from plants. A representative botanical agent(s) may include, but is not limited to, *Vanilla planifolia* Fruit Extract, *Avena sativa* (Oat) Kernel Oil, *Lavandula angustifolia* (Lavender) Oil, *Aloe barbadensis* (Aloe Vera) Leaf Extract, *Bambusa vulgaris* (Bamboo) Water, and/or *Arnica montana* Flower Extract.

A representative antioxidant(s) may include, but is not limited to, tocopherol.

A representative emulsifier(s) may include, but is not limited to, cetyl esters.

A representative vitamin(s) may include, but is not limited to, Tocopheryl Acetate (Vitamin E Acetate), Beta-Sitosterol, Ascorbyl Palmitate (Vitamin C Palmitate) and/or Phytonadione (Vitamin K1).

A representative humectant(s) may include, but is not limited to, Glycerin, *Crambe abyssinica* (Abyssinian) Seed Oil and Sodium PCA. Glycerin may be a plant derived Glycerin which has natural moisturizing factors beneficial to pets. *Crambe abyssinica* (Abyssinian) Seed Oil is a natural seed oil with an ultra-light, non-greasy feel which absorbs quickly and provides superior moisturizing benefits to pets.

A representative film forming agent(s) may include, but is not limited to, Citrus *Aurantium dulcis* (Orange) Peel Wax and/or Triethoxycaprylylsilane.

A representative calming agent(s) may include, but is not limited to, allantoin.

A representative sweetener(s), may include, but is not limited to, sucralose.

A representative colorant(s) may include, but is not limited to, Iron Oxide (Yellow) (CI #77492), Mica, Titanium Dioxide (CAS 13663-67-7), Red 33 (CI #17200), Iron Oxide (mineral origin) (CI #77491), Red 7 (CI #15850, CAS 5281-04-9), Red 6 (CI #15850, CAS 17582-98-1), Titanium Dioxide (CI #77891, CAS 13463-67-70), and/or Black Iron Oxide (CI #77499).

A representative lip plumping agent(s) may include, but is not limited to, sodium hyaluronate, *Arnica montana* flower extract and/or Phytonadione (Vitamin K1). Representatively, in one embodiment, sodium hyaluronate may be in an amount of from about 0.01% to less than 0.1% by weight, for example, 0.01% to 0.09% by weight, *Arnica montana* Flower Extract may be in an amount of from about 0.01% to less than 0.1% by weight, for example, 0.01% to 0.09% by weight, and Phytonadione (Vitamin K1) may be in an amount of from about 0.01% to less than 0.1% by weight, for example, from 0.01% to 0.09% by weight, of the composition.

For example, in one embodiment, a lip care composition, for example, a lip stick or lip balm may be formed by combining or mixing two or more of the following ingredients or agents in the amounts (listed as percentage by weight of the total composition) as follows: at least 30% by weight Vegetable Oil (Virgin Olive Oil Based), 10% to 30% by weight Paraffinum Liquidum, 10% to 30% by weight *Helianthus annuus* (Sunflower) Seed Oil, 1% to 3% by weight *Ricinus communis* (Castor) Seed Oil, 10% to 30% by weight *Butyrospermum parkii* (Shea) Butter Extract Unsaponifiable, 0.1% to 0.3% by weight Mango (*Mangifera indica*) Butter, 0.1% to 0.3% by weight Jojoba Esters, 0.1% to 0.3% by weight Hydrogenated Vegetable Oil, 0.01% to 0.1% by weight Squalene, 0.01% to 0.1% by weight *Theobroma grandiflorum* (Cupuacu) Seed Butter, 0.01% to 0.1% by weight *Schinziophyton rautanenii* (Mongongo) Seed Oil, 0.01% to 0.1% by weight *Persea gratissima* (Avocado) Oil, 0.01% to 01% by weight *Orbignya oleifera* Seed (Babassu Nut) Oil, 0.01% to 0.1% by weight Hydrogenated *Moringa* Oil Esters, 0,01% to 01% by weight *Punica granatum* (Pomegranate) Seed Oil, 0.01% to 0.1% by weight *Oenothera biennis* (Evening Primrose) Oil, 0.01% to 0.1% by weight *Camellia kissi* (Sasanqua) Seed Oil, 3% to 10% by weight Ozokerite Wax, 3% to 10% by weight Beeswax, 1% to 3% by weight Nylon-11, 0.01% to 0.3% by weight *Euphorbia cerifera* (Candelilla) Wax, 0.01% to 0.3% by weight *Copernicia cerifera* (Carnauba) Wax, 0.3% to 1% by weight Tocopherol, 0.3% to 1% by weight Cetyl Esters, 0.3% to 1% *Vanilla planifolia* Fruit Extract, 0.3% to 1% by weight *Avena Sativa* (Oat) Kernel Oil, 0.01% to 0,1% by weight *Lavandula angustifolia* (Lavender) Oil, 0.01% to 0.1% by weight *Aloe barbadensis* (Aloe Vera) Leaf Extract, 0.01% to 0.1% by weight *Bambusa vulgaris* (Bamboo) Water, 0.01% to 0.1% by weight *Arnica montana* Flower Extract, 0.01% to 0.3% by weight Tocopheryl Acetate (Vitamin E Acetate), 0.01% to 0.1% by weight Beta-Sitosterol, 001% to 0.1% by weight Ascorbyl Palmitate (Vitamin C Palmitate), 0.01% to 0.1% by weight Phytonadione (Vitamin K1), 0.01% to 0.1% by weight *Crambe abyssinica* (Abyssinian) Seed Oil, 0,01% to 0.1% by weight Sodium Hyaluronate, 0.01% to 0.1% by weight Citrus *Aurantium dulcis* (Orange) Peel Wax, 0.01% to 0.1% by weight Triethoxycaprylylsilane, 0.01% to 0.1% by weight Allantoin, 0.01% to 0.1% by weight Sucralose, 0.01% to 0.1% by weight Iron Oxide (CI #77492), 0.01% to 0.1% by weight Mica, 0.01% to 0.1% by weight Titanium Dioxide (CAS 13663-67-7), 0.01% to 0.1% by weight Red 33 (CI #17200), 0.01% to 0.1% by weight Iron Oxide (CI #77491), 0.01% to 0.1% by weight CI 15850, 0.01% to 0.1% by weight Red 6 (CI #15850), 0.01% to 0.1% by weight CI 77891 (Titanium Dioxide), and/or 0.01% to 0.1% by weight Black Iron Oxide CI 77499.

Lip Scrub

In other embodiments, the composition may by a lip scrub. The composition may be considered a lip scrub in that it includes an abrasive, or other exfoliating agent, specifically designed to remove dead skin cells from the lips. Exfoliation of the lips is believed to enhance absorption of agents (e.g., moisturizing agents) because it removes dead skin cells which can prevent absorption, or otherwise act as a barrier, to treatment or lip care agents (e.g., moisturizing agents).

The lip scrub may include a synergistic combination of one or more of an abrasive(s), emollient(s), thickeners(s), botanical(s), antioxidant(s), plumping agent(s), emulsifier(s), vitamin(s), humectant(s), film former(s) and/or preservative(s).

In one embodiment, the composition balances one or more emollient(s), thickener(s), abrasive(s), botanical(s), antioxidant(s), plumping agent(s), emulsifiers(s), vitamin(s), humectant(s), film formers(s) and/or preservative(s) in amounts sufficient to provide a composition that effectively nourishes, moisturizes, restores, treats, plumps, scrubs and/or exfoliates the lips when it is applied.

Representatively, in one aspect, the lip care composition may be a lip scrub which includes, among other ingredients, an exfoliant or abrasive designed to gently exfoliate the lips by buffing away dead, dry skin cells. The exfoliating or abrasive agent may be an agent other than sugar, and which is gentler than sugar at exfoliating the lips. In one aspect, the exfoliating or abrasive agent may be *Citrus limon* (Lemon) Peel Powder. *Citrus limon* (Lemon) Peel Powder may consist of granules of powder obtained from the peel of a lemon. The granules are incorporated into the lip scrub such that when the lip scrub is applied or rubbed onto the lips, it acts as a gentle abrasive that can remove dead skin cells from the lips.

In addition, the lip scrub may further include, among others, ingredients such as paraffin, shea butter, beeswax, essential oils, vitamin C & E and/or bamboo water, which help to exfoliate, moisturize, treat, restore, nourish or otherwise improve the condition of the user's lips. Additionally, the composition may include ingredients such as sodium hyaluronate, *Arnica montana* flower extract and/or Vitamin K, which are synergistically combined to provide a lip plumping effect when applied to the lips. In addition, it should be recognized that the composition may be in any form suitable for application to the user's lips, and is not limited to any particular form and/or shaped container. For example, the lip scrub may be a lip balm, lip stick, lip cream, lip gel, lip gloss, or the like, that can be used in any size/shape container. The composition may be applied to the lips directly, or rubbed on the user's finger and then applied to the lips.

Representatively, in one aspect, a balanced lip scrub composition includes from about 60 percent (%) to about 100% by weight emollient(s), from about 6% to 21% by weight thickening agent(s), from about 3% to 13% by weight botanical agent(s), from about 3% to 10% abrasive, from about 0.3% to 1% by weight antioxidant(s), from about 0.5% to 2% by weight emulsifier(s), from about 2.5% to 6% a preservative, from about 0.1% to 0.5% by weight vitamin(s), from about 0.02% to 0.2% by weight humectant(s), and/or from about 1.3% to 4.1% by weight film forming agent(s). In addition, a combination of one or more of plumping agent(s) may be included in the composition in an amount of about 0.01% to 0.27% to effectively provide a lip plumping effect. In other embodiments, the composition can contain any one or more of the agents or ingredients disclosed herein, in any amounts and any combinations sufficient to exfoliate, nourish, moisturize, restore, treat and/or plumps the lips when it is applied.

A representative emollient(s) may include, but is not limited to, vegetable oil (virgin olive oil based), paraffinum liquidum, *Helianthus annuus* (Sunflower) Seed Oil, Butyrosperum *Parkii* (Shea Butter) Unsaponafiables, polyglycerin-3, Mango (*Mangifera indica*) Butter, *Cocos nucifera* (Coconut) Oil, *Theobroma grandiflorum* (Cupuacu) Seed Butter, Schinzeiophyton *Rautanenii* (Mongongo) Seed Oil, *Persa gratissima* (Avocado) Oil, Obignya *Oleifera* Seed (Babassu Nut) Oil, Hydrogenated *Moringa* Oil Esters, *Punica granatum* (Pomegranate) Seed Oil, *Oenothera biennis* (Evening Primrose) Oil, and/or *Camellia kissi* (Sasanqua) Seed Oil.

A representative thickening agent(s) may include, but is not limited to, Ozokerite Wax, Beeswax, Mango (*Mangifera indica*) Butter, and/or *Euphorbia cerifera* (Candelilla) Wax.

A representative botanical agent(s) may include, but is not limited to, *Oryza sativa* (Rice) Powder, Jojoba Esters, *Vanilla planifolia* Fruit Extract, *Avena sativa* (Oat) Kernel Oil, *Lavandula angustifolia* (Lavender) Oil, *Aloe barbadensis* (*Aloe vera*) Leaf Extract, *Bambusa vulgaris* (Bamboo) Water, and/or *Arnica montana* Flower Extract.

A representative abrasive(s) may include, but is not limited to, *Citrus limon* Peel Powder and/or *Oryza sativa* (Rice) Powder. The abrasive(s) may be combined in critical amounts which have been found to maximize exfoliation of the lips. Representatively, in one embodiment, *Citrus limon* Peel Powder may be in an amount of from about 2.5% to 10% by weight, for example, 3% to 9.99% by weight, and/or *Oryza sativa* (Rice) Powder may be in an amount of from about 2.5% to 10% by weight, for example, 3% to 9.99% by weight, of the composition.

A representative antioxidant(s) may include, but is not limited it, tocopherol.

A representative emulsifier(s) may include, but is not limited to, cetyl esters and/or glyceryl caprylate.

A representative preservative(s) may include, but is not limited to, Hydroxyacetophenone (i.e., Ethanone).

A representative vitamin(s) may include, but is not limited to, Tocopheryl Acetate (Vitamin E Acetate), Ascorbyl Palmitate (Vitamin C Palmitate) and/or Phytonadione (Vitamin K1).

A representative humectant(s) may include, but is not limited to, *Crambe abyssinica* (Abyssinian) Seed Oil and/or Sodium Hyaluronate.

A representative film forming agent(s) may include, but is not limited to, *Acacia decurrens* (*Mimosa*) Flower Wax, *Helianthus annuus* (Sunflower) Seed Wax and/or Citrus *Aurantium dulcis* (Orange) Peel Wax.

A representative plumping agent(s) may include, but is not limited to, as sodium hyaluronate, *Arnica montana* flower extract and/or Phytonadione (Vitamin K1). The plumping agents may be combined in critical amounts which have been found to maximize the lip plumping effect. Representatively, in one embodiment, sodium hyaluronate may be in an amount of from about 0.01% to less than 0.1% by weight, for example, 0.01% to 0.09% by weight, *Arnica montana* Flower Extract may be in an amount of from about 0.01% to less than 0.1% by weight, for example, 0.01% to 0.09% by weight, and Phytonadione (Vitamin K1) may be in an amount of from about 0.01% to less than 0.1% by weight, for example, from 0.01% to 0.09% by weight, of the composition.

For example, in one embodiment, the lip scrub may be formed by combining or mixing two or more ingredients or agents in the amounts (listed as percentage by weight of the total composition) as follows: at least 30% by weight Vegetable Oil (Virgin Olive Oil Based), 10% to 30% Paraffinum Liquidum, 10% to 30% by weight *Helianthus annuus* (Sunflower) Seed Oil, 10% to 30% by weight *Butyrospermum parkii* (Shea Butter) Unsaponifiables, 0.1% to 0.3% by weight Polyglycerin-3, 0.1% to 0.3% by weight Mango (*Mangifera indica*) Butter, 0.1% to 0.3% by weight *Cocos nucifera* (Coconut) Oil, 0.01% to 0.1% by weight *Theobroma grandiflorum* (Cupuacu) Seed Butter, 0.01% to 0.1% by weight *Schinziophyton rautanenii* (Mongongo) Seed Oil, 0.01% to 0.1% by weight *Persea gratissima* (Avocado) Oil, 0.01% to 0.1% by weight *Orbignya oleifera* Seed (Babassu Nut) Oil, 0.01% to 0.1% by weight Hydrogenated *Moringa* Oil Esters, 0.01% to 0.1% by weight *Punica granatum* (Pomegranate) Seed Oil, 0.01% to 0.1% by weight *Oenothera biennis* (Evening Primrose) Oil, 0.01% to 0.1% by weight *Camellia kissi* (Sasanqua) Seed Oil, 3% to 10% by weight Ozokerite Wax, 3% to 10% by weight Beeswax, 0,1% to 03% by weight Mango (*Mangifera indica*) Butter, 0.1% to 0.3% by weight *Euphorbia cerifera* (Candelilla) Wax, 3% to 10% by weight *Citrus limon* Peel Powder, 0.3% to 1% by weight Tocopherol, 0.3% to 1% by weight Glyceryl Caprylate, 0.3% to 1% by weight Cetyl Esters, 0.3% to 0.7% by weight Hydroxyacetophenone (aka Ethanone), 3% to 10% by weight *Oryza sativa* (Rice) Powder, 3% to 10% by weight Jojoba Esters, 0.3% to 1% by weight *Vanilla planifolia* Fruit Extract, 0.3% to 1% by weight *Avena sativa* (Oat) Kernel Oil, 0.1% to 03% by weight *Aloe barbadensis* (*Aloe vera*) Leaf Extract, 0.01% to 0.1% by weight *Lavandula angustifolia* (Lavender) Oil, 0.01% to 0.1% by weight *Bambusa vulgaris* (Bamboo) Water, 0.01% to 0.1% by weight *Arnica montana* Flower Extract, 0.1% to 0.3% by weight Tocopheryl Acetate (Vitamin E Acetate), 0.01% to 0.1% by weight Ascorbyl Palmitate (Vitamin C Palmitate), 0.01% to 0.1% by weight Phytonadione (Vitamin K1), 0.01% to 0.1% by weight *Crambe abyssinica* (Abyssinian) Seed Oil, 0.01% to 0.1% by weight Sodium Hyaluronate, 1% to 3% by weight *Acacia decurrens* (*Mimosa*) Flower Wax, 0.3% to 1% by weight *Helianthus annuus* (Sunflower) Seed Wax, and/or 0.01% to 0.1% by weight Citrus *Aurantium dulcis* (Orange) Peel Wax.

Other ingredients or agents included in the composition that may not be specifically discussed above are included and described in reference to the exemplary formulations set forth below. In addition, it should further be understood that although the agents described herein are categorized according to a single function, many have multiple functions and therefore may be understood to be included under other functional categories than those listed herein.

The following specific examples set forth exemplary compositions that may be topically applied to a subject (e.g. the lips of a user). The ingredient amounts disclosed in the following examples are in effective amounts suitable for moisturizing, treating, restoring, nourishing, scrubbing, plumping or otherwise improving the condition of the area to which the composition is applied. The composition may have one of the following exemplary formulations:

Example 1

| Percent | Ingredient (INCI Name) | Function |
| --- | --- | --- |
| 30.00-100.00 | Vegetable Oil (Virgin Olive Oil Based) | Emollient |
| 10.00-29.99 | Paraffinum Liguidum | Emollient |
| 10.00-29.99 | Helianthus Annuus (Sunflower) Seed Oil | Emollient |
| 10.00-29.99 | Butyrospermum Parkii (Shea Butter) Unsaponifiables | Emollient |
| 3.00-9.99 | Ozokerite Wax | Thickener |
| 3.00-9.99 | Beeswax | Thickener |
| 1.00-2.99 | Nylon-11 | Emollient |
| 0.30-0.99 | Tocopherol | Antioxidant |
| 0.30-0.99 | Cetyl Esters | Emulsifier |
| 0.30-0.99 | Butyrospermum Parkii (Shea Butter) Extract | Emollient |
| 0.30-0.99 | Avena Sativa (Oat) Kernel Oil | Botanical |
| 0.10-0.29 | Tocopheryl Acetate (Vitamin E Acetate) | Vitamin |
| 0.10-0.29 | Mango (Mangifera Indica) Butter | Emollient |
| 0.10-0.29 | Jojoba Esters | Botanical |
| 0.10-0.29 | Euphorbia Cerifera (Candelilla) Wax | Thickener |
| 0.10-0.29 | Copernicia Centers (Carnauba) Wax | Thickener |
| 0.10-0.29 | Cocos Nucifera (Coconut) Oil | Emollient |
| 0.10-0.29 | Aloe Barbadensis (Aloe Vera) Leaf Extract | Botanical |
| 0.01-0.09 | Melaleuca Alternifolia (Tea Tree) Leaf Oil | Emollient |
| 0.01-0.09 | Ascorbyi Palmitate (Vitamin C Palmitate) | Vitamin |
| 0.01-0.09 | Theobroma Grandiflorum (Cupuacu) Seed Butter | Emollient |
| 0.01-0.09 | Schinziophyton Rautanenii (Mongorigo) Seed Oil | Emollient |
| 0.01-0.09 | Persea Gratissirna (Avocado) Oil | Emollient |
| 0.01-0.09 | Orbignya Oleifera Seed (Babassu Nut) Oil | Emollient |
| 0.01-0.09 | Hydrogenated Moringa Oil Esters | Emollient |
| 0.01-0.09 | Crambe Abyssinica (Abyssinian) Seed Oil | Humectant |
| 0.01-0.09 | Punica Granatum (Pomegranate) Seed Oil | Emollient |
| 0.01-0.09 | Oenothera Biennis (Evening Primrose) Oil | Emollient |
| 0.01-0.09 | Camellia Kissi (Sasangua) Seed Oil | Emollient |
| 0.01-0.09 | Citrus Aurantium Dulcis (Orange) Peel Wax | Film Former |
| 0.01-0.09 | Allantoin | Calming Agent |
| 0.01-0.09 | Sucralose | Sweetener |
| 0.01-0.09 | Sodium Hyaluronate | Humectant/Plumping |
| 0.01-0.09 | Bambusa Vulgaris (Bamboo) Water | Botanical |
| 0.01-0.09 | Arnica Montana Flower Extract | Botanical/Plumping |
| 0.01-0.09 | Phytonadione (Vitamin K1) | Vitamin/Plumping |

Example 2

| Percent | Ingredient (INCI Name) | Function |
|---|---|---|
| 30.00-100.00 | Vegetable Oil (Virgin Olive Oil Based) | Emollient |
| 10.00-29.99 | Paraffinum Liquidum | Emollient |
| 10.00-29.99 | Helianthus Annuus (Sunflower) Seed Oil | Emollient |
| 10.00-29.99 | Butyrospermum Parkii (Shea) Butter Linsaponifiable | Emollient |
| 3.00-9.99 | Ozokerite Wax | Thickener |
| 3.00-9.99 | Beeswax | Thickener |
| 1.00-2.99 | Nylon-11 | Thickener |
| 1.00-2.99 | Ricinus Communis (Castor) Seed Oil | Emollient |
| 0.30-0.99 | Vanilla Planifolia Fruit Extract | Botanical |
| 0.30-0.99 | Cetyl Esters | Emulsifier |
| 0.30-0.99 | Butyrospermum Parkii (Shea) Butter Extract | Emollient |
| 0.30-0.99 | Avena Sativa (Oat) Kernel Oil | Botanical |
| 0.10-0.29 | Tocopheryl Acetate (Vitamin E Acetate) | Vitamin |
| 0.10-0.29 | Mango (Mangifera Indica) Butter | Emollient |
| 0.10-0.29 | Jojoba Esters | Emollient |
| 0.10-0.29 | Euphorbia Cerifera (Candelilla) Wax | Thickener |
| 0.10- 0.29 | Copernicia Cerifera (Carnauba) Wax | Thickener |
| 0.10-0.29 | Hydrogenated Vegetable Oil | Emollient |
| 0.10-0.29 | Tocopherol | Antioxidant |
| 0.01-0.09 | Iron Oxide (CI# 77492) | Colorant |
| 0.01-0.09 | Beta-Sitosterol | Vitamin |
| 0.01-0.09 | Mica | Colorant |
| 0.01-0.09 | Titanium Dioxide (CAS 13663-67-7) | Colorant |
| 0.01-0.09 | Lavandula Angustifolia (Lavender) Oil | Botanical |
| 0.01-0.09 | Red 33 (CI# 017200) | Colorant |
| 0.01-0.09 | Squalene | Emollient |
| 0.01-0.09 | Aloe Barbadensis (Aloe Vera) Leaf Extract | Botanical |
| 0.01-0.09 | Iron Oxide (CI# 77491) | Colorant |
| 0.01-0.09 | Ascorbyl Palmitate (Vitamin C Paimitate) | Vitamin |
| 0.01-0.09 | Sucrelose | Sweetener |
| 0.01-0.09 | Theobroma Granditiorurn (Cupuacu) Seed Butter | Emoiient |
| 0.01-0.09 | Schinziophyton Rautarienil (Mongongo) Seed Oil | Emollient |
| 0.01-0.09 | Parses Gratissima (Avocado) Oil | Emollient |
| 0.01-0.09 | Orbignya Oleifera Seed (Babassu Nut) Oil | Emollient |
| 0.01-0.09 | Hydrogenated Moringa Oil Esters | Emollient |
| 0.01-0.09 | Crambe Abyssinica (Abyssinian) Seed Oil | Humectant |
| 0.01-0.09 | Punica Granatum (Pomegranate) Seed Oil | Emollient |
| 0.01-0.09 | Oenothera Biennis (Evening Primrose) Oil | Emollient |
| 0.01-0.09 | Camellia Kissi (Sasanqua) Seed Oil | Emollient |
| 0.01-0.09 | Citrus Aurantiurn Dulcis (Orange) Peel Wax | Film Former |
| 0.01-0.09 | Allantoin | Calming Agent |
| 0.01-0.09 | Red 7 | Colorant |
| 0.01-0.09 | Red 6 | Colorant |
| 0.01-0.09 | Titanium Dioxide (CI# 77891) (CAS 13463-57-70) | Colorant |
| 0.01-0.09 | Triethoxycaprylylsilane | Film Former |
| 0.01-0.09 | Sodium Hyalumnate | Humectant/Plumping |
| 0.01-0.09 | Barribusa Vulgaris (Bamboo) Water | Botanical |
| 0.01-0.09 | Arnica Montana Rower Extract | Botanical/Plumping |
| 0.01-0.09 | Phytonadione (Vitamin K1) | Vitamin/Plumping |
| 0.01-0.09 | Black Iron Oxide (CI# 77499) | Colorant |

Example 3

| Percent | Ingredient (INCI Name) | Function |
|---|---|---|
| 30.00-100.00 | Vegetable Oil (Virgin Olive Of Based) | Emollient |
| 10.00-29.99 | Paraffinum Liguidum | Emollient |
| 10.00-29.99 | Helianthus Annuus (Sunflower) Seed Oil | Emollient |
| 10.00-29.99 | Butyrospermum Parkii (Shea) Butter Unsaponifiables | Emollient |
| 3.00-9.99 | Ozokerite Wax | Thickener |
| 3.00-9.99 | Beeswax | Thickener |
| 3.00-9.99 | Oriza Saliva (Rice) Powder | Abrasive |
| 3.00-9.99 | Citrus Limon Peel Powder | Abrasive |
| 3.00-9.99 | Jojoba Esters | Botanical |
| 1.00-2.99 | Acacia Decurrens (Mimosa) Flower Wax | Film Former |
| 0.30-0.99 | Vanilla Planifolia Fruit Extract | Botanical |
| 0.30-0.99 | Glyceryl Caprylate | Emulsifier |
| 0.30-0.99 | Helianthus Annuus (Sunflower) Seed Wax | Film Former |
| 0.30-0.99 | Tocopherol | Antioxidant |
| 0.5 | Hydroxyacetophenone (aka Ethanone) | Preservative |
| 0.30-0.99 | Cetyl Esters | Emulsifier |
| 0.30-0.99 | Avena Sativa (Oat) Kernel Oil | Botanical |

-continued

Example 3

| Percent | Ingredient (INCI Name) | Function |
|---|---|---|
| 0.10-0.29 | Tocopheryl Acetate (Vitamin E Acetate) | Vitamin |
| 0.10-0.29 | Polyglycerin-3 | Emollient |
| 0.10-0.29 | Mango (Mangitera Indical) Butter | Emollient |
| 0.10-0.29 | Euphorbia Cerifera (Candelilla) Wax | Thickener |
| 0.10-0.29 | Copernicia Centers (Carnauba) Wax | Thickener |
| 0.10-0.29 | Cocos Nucitera (Coconut) Of | Emollient |
| 0.10-0.29 | Aloe Barbadensis (Aloe Vera) Leaf Extract | Botanical |
| 0.01-0.09 | Lavandula Arigustifolia (Lavender) Oil | Botanical |
| 0.01-0.09 | Ascorbyl Palmitate (Vitamin C Pairnitate) | Vitarilin |
| 0.01-0.09 | Theobroma Grandiflorurn (Cupuacu) Seed Butter | Emollient |
| 0.01-0.09 | Schinziophyton Rautanenii (Mongongo) Seed Oil | Emollient |
| 0.01-0.09 | Persea Gratissirna (Avocado) Oil | Emollient |
| 0.01-0.09 | Orbignya Oleitera Seed (Babassu Nut) Oil | Emollient |
| 0.01-0.09 | Hydrogenated Moringa Oil Esters | Emollient |
| 0.01-0.09 | Crambe Abyssinica (Abyssinian) Seed Oil | Humectant |
| 0.01-0.09 | Punica Granatum (Pomegranate) Seed Oil | Emollient |
| 0.01-0.09 | Oenothera Biennis (Evening Primrose) Oil | Emollient |
| 0.01-0.09 | Camellia Kissi (Sasanqua) Seed Oil | Emollient |
| 0.01-0.09 | Citrus Aurantium Dulcis (Orange) Peel Wax | Film Former |
| 0.09 | Sodium Hyaluronate | Humectant/Plumping |
| 0.01-0.09 | Bambusa Vulgaris (Bamboo) Water | Botanical |
| 0.01-0.09 | Arnica Montana Rower Extract | Botanical/Plumping |
| 0.01-0.09 | Phytonariione (Vitamin K1) | Vitamin/Plumping |

It should be appreciated that reference throughout this specification to "one embodiment" or "an embodiment" means that a particular feature, structure or characteristic described in connection with the embodiment is included in at least one embodiment of the present invention. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the invention.

In the foregoing specification, the invention has been described with reference to specific embodiments thereof. It will, however, be evident that various modifications and changes can be made thereto without departing from the broader spirit and scope of the invention as set forth in the appended claims. The specification and drawing are, accordingly, to be regarded in an illustrative rather than a restrictive sense.

The invention claimed is:

1. A lip care composition comprising:
an emollient;
a thickener comprising a combination of thickeners in an amount of from 5% to 25% by weight of the total composition;
an antioxidant comprising tocopherol in an amount of 0.1% to 0.9% by weight of the total composition;
an emulsifier;
a botanical comprising a combination of botanicals in an amount of from 0.6% to 2.5% by weight of the total composition;
a vitamin comprising a combination of a vitamins in an amount of from 0.1% to 0.6% by weight of the total composition;
a humectant in an amount of from 0.01% to 0.09% by weight of the total composition;
a film former in an amount of from 0.01% to 0.09% by weight of the total composition;
a calming agent in an amount of from 0.01% to 0.09% by weight of the total composition;
a sweetener; and
a lip plumper, the lip plumper comprising Sodium Hyaluronate in an amount of from 0.01% to 0.1% by weight, *Arnica montana* Flower Extract in an amount of from 0.01% to 0.1% by weight and Phytonadione in an amount of from 0.01% to 0.1% by weight of the total composition.

2. The lip care composition of claim 1 further comprising a colorant.

3. The lip care composition of claim 1 wherein the emollient is in an amount of at least 30% by weight of the total composition.

4. The lip care composition of claim 1 wherein the antioxidant is in an amount of from 0.1% to 0.3% by weight of the total composition.

5. The lip care composition of claim 1 wherein the emulsifier is in an amount of from 0.3% to 1% by weight of the total composition.

6. The lip care composition of claim 1 wherein the emollient comprises a combination of Vegetable Oil, Paraffinum Liquidum, *Helianthus annuus* Seed Oil, *Ricinus communis* Seed Oil, *Butyrospermum parkii* (Shea) Butter Extract Unsaponifiables, Mango Butter, Jojoba Esters, Hydrogenated Vegetable Oil, Squalene, *Theobroma grandiflorum* (Cupuacu) Seed Butter, *Schinziophyton rautanenii* (Mongongo) Seed Oil, *Persea Gratissima* (Avocado) Oil, *Orbignya oleifera* Seed (Babassu Nut) Oil, Hydrogenated *Moringa* Oil Esters, *Punica granatum* (Pomegranate) Seed Oil, *Oenothera biennis* (Evening Primrose) Oil, and *Camellia kissi* (Sasanqua) Seed Oil.

7. The lip care composition of claim 1 wherein the thickener comprises a combination of Ozokerite Wax, Beeswax, Nylon-11, *Euphorbia Cerifera* Wax and *Copernicia Cerifera* Wax.

8. The lip care composition of claim 1 wherein the emulsifier comprises Cetyl Esters.

9. The lip care composition of claim 1 wherein the botanical comprises a combination of *Vanilla planifolia* Fruit Extract, *Avena sativa* Kernel Oil, *Lavandula angustifolia* Oil, *Aloe barbadensis* Leaf Extract and *Bambusa vulgaris* Water.

10. The lip care composition of claim 1 wherein the vitamin comprises a combination of Tocopheryl Acetate, Beta-Sitosterol and Ascorbyl Palmitate.

11. The lip care composition of claim 1 wherein the humectant comprises *Crambe Abyssinica* Seed Oil.

12. The lip care composition of claim 1 wherein the film former comprises Citrus *Aurantium dulcis* Peel Wax.

13. The lip care composition of claim 1 wherein the calming agent comprises Allantoin.

14. The lip care composition of claim 1 wherein the sweetener comprises Sucralose.

15. A composition comprising:
- at least 30% by weight Vegetable Oil;
- 10% to 30% by weight Paraffinum Liquidum;
- 10% to 30% by weight *Helianthus annuus* Seed Oil;
- 10% to 30% by weight *Butyrospermum parkii* Unsaponifiables;
- 3% to 10% by weight Ozokerite Wax;
- 3% to 10% by weight Beeswax;
- 1% to 3% by weight Nylon-11;
- 0.3% to 1% by weight Tocopherol;
- 0.3% to 1% by weight Cetyl Esters;
- 0.3% to 1% by weight *Butyrospermum parkii* Extract;
- 0.3% to 1% by weight *Avena sativa* Kernel Oil;
- 0.1% to 0.3% by weight Tocopheryl Acetate;
- 0.1% to 0.3% by weight Mango Butter;
- 0.1% to 0.3% by weight Jojoba Esters;
- 0.1% to 0.3% by weight *Euphorbia cerifera* Wax;
- 0.1% to 0.3% by weight *Copernicia cerifera* Wax;
- 0.1% to 0.3% by weight *Cocos nucifera* Oil;
- 0.1% to 0.3% by weight *Aloe barbadensis* Leaf Extract;
- 0.01% to 0.1% by weight *Melaleuca alternifolia* Leaf Oil;
- 0.01% to 0.1% by weight Ascorbyl Palmitate;
- 0.01% to 0.1% by weight *Theobroma grandiflorum* Seed Butter;
- 0.01% to 0.1% by weight *Schinziophyton rautanenii* Seed Oil;
- 0.01% to 0.1% by weight *Persea gratissima* Oil;
- 0.01% to 0.1% by weight *Orbignya oleifera* Seed Oil;
- 0.01% to 0.1% by weight Hydrogenated *Moringa* Oil Esters;
- 0.01% to 0.1% by weight *Crambe abyssinica* Seed Oil;
- 0.01% to 0.1% by weight *Punica granatum* Seed Oil;
- 0.01% to 0.1% by weight *Oenothera biennis* Oil;
- 0.01% to 0.1% by weight *Camellia kissi* Seed Oil;
- 0.01% to 0.1% by weight Citrus *Aurantium dulcis* Peel Wax;
- 0.01% to 0.1% by weight Allantoin;
- 0.01% to 0.1% by weight Sucralose;
- 0.01% to 0.1% by weight Sodium Hyaluronate;
- 0.01% to 0.1% by weight *Bambusa vulgaris* Water;
- 0.01% to 0.1% by weight *Arnica montana* Flower Extract; and
- 0.01% to 0.1% by weight Phytonadione.

16. A composition comprising:
- at least 30.00 by weight Vegetable Oil;
- 10% to 30% by weight Paraffinum Liquidum;
- 10% to 30% by weight *Helianthus annuus* Seed Oil;
- 10% to 30% by weight *Butyrospermum parkii* Butter Unsaponifiable;
- 3% to 10% by weight Ozokerite Wax;
- 3% to 10% by weight Beeswax;
- 1% to 3% by weight Nylon-11;
- 1% to 3% by weight *Ricinus communis* Seed Oil;
- 0.3% to 1% by weight *Vanilla planifolia* Fruit Extract;
- 0.3% to 1% by weight Cetyl Esters;
- 0.3% to 1% by weight *Butyrospermum parkii* Butter Extract;
- 0.3% to 1% by weight *Avena sativa* Kernel Oil;
- 0.1% to 0.3% by weight Tocopheryl Acetate;
- 0.1% to 0.3% by weight Mango Butter;
- 0.1% to 0.3% by weight Jojoba Esters;
- 0.1% to 0.3% by weight *Euphorbia cerifera* Wax;
- 0.1% to 0.3% by weight *Copernicia cerifera* Wax;
- 0.1% to 0.3% by weight Hydrogenated Vegetable Oil;
- 0.1% to 0.3% by weight Tocopherol;
- 0.01% to 0.1% by weight Yellow Iron Oxide;
- 0.01% to 0.1% by weight Beta-Sitosterol;
- 0.01% to 0.1% by weight Mica;
- 0.01% to 0.1% by weight a first Titanium Dioxide;
- 0.01% to 0.1% by weight *Lavandula angustifolia* Oil;
- 0.01% to 0.1% by weight a colorant comprising Red 33;
- 0.01% to 0.1% by weight Squalene;
- 0.01% to 0.1% by weight *Aloe barbadensis* Leaf Extract;
- 0.01% to 0.1% by weight Red Iron Oxide;
- 0.01% to 0.1% by weight Ascorbyl Palmitate;
- 0.01% to 0.1% by weight Sucralose;
- 0.01% to 0.1% by weight *Theobroma grandiflorum* Seed Butter;
- 0.01% to 0.1% by weight *Schinziophyton rautanenii* Seed Oil;
- 0.01% to 0.1% by weight *Persea gratissima* Oil;
- 0.01% to 0.1% by weight *Orbignya oleifera* Seed Oil;
- 0.01% to 0.1% by weight Hydrogenated *Moringa* Oil Esters;
- 0.01% to 0.1% by weight *Crambe abyssinica* Seed Oil;
- 0.01% to 0.1% by weight *Punica granatum* Seed Oil;
- 0.01% to 0.1% by weight *Oenothera biennis* Oil;
- 0.01% to 0.1% by weight *Camellia kissi* Seed Oil;
- 0.01% to 0.1% by weight Citrus *Aurantium dulcis* Peel Wax;
- 0.01% to 0.1% by weight Allantoin;
- 0.01% to 0.1% by weight Red 7;
- 0.01% to 0.1% by weight Red 6;
- 0.01% to 0.1% by weight a second Titanium Dioxide;
- 0.01% to 0.1% by weight Triethoxycaprylylsilane;
- 0.01% to 0.1% by weight Sodium Hyaluronate;
- 0.01% to 0.1% by weight *Bambusa vulgaris* Water;
- 0.01% to 0.1% by weight *Arnica montana* Flower Extract;
- 0.01% to 0.1% by weight Phytonadione; and
- 0.01% to 0.1% by weight Black Iron Oxide.

* * * * *